(12) United States Patent
Warren et al.

(10) Patent No.: US 9,387,271 B2
(45) Date of Patent: Jul. 12, 2016

(54) TECHNIQUES FOR INFUSING ION CLUSTERS INTO A TARGET ENVIRONMENT

(75) Inventors: Wallace Weston Warren, Jefferson City, MO (US); Tim Zwijack, Camdenton, MO (US)

(73) Assignee: Tim Zwijack, Camdenton, MO (US)

( * ) Notice: Subject to any disclaimer, the term of this patent is extended or adjusted under 35 U.S.C. 154(b) by 0 days.

(21) Appl. No.: 13/358,646

(22) Filed: Jan. 26, 2012

(65) Prior Publication Data
US 2013/0195715 A1    Aug. 1, 2013

(51) Int. Cl.
*A61L 9/00* (2006.01)
*A61L 9/20* (2006.01)
*A61L 9/22* (2006.01)
*F24F 3/16* (2006.01)

(52) U.S. Cl.
CPC . *A61L 9/205* (2013.01); *A61L 9/22* (2013.01); *F24F 3/16* (2013.01); *F24F 2003/1628* (2013.01); *F24F 2003/1682* (2013.01); *F24F 2221/14* (2013.01)

(58) Field of Classification Search
CPC ............. A61L 9/22; A61L 9/205; F24F 3/16; F24F 2003/1628; F24F 2003/1682; F24F 2221/14
USPC .................................. 422/186.04, 186.3, 121
See application file for complete search history.

(56) References Cited

U.S. PATENT DOCUMENTS

| | | | |
|---|---|---|---|
| 3,422,263 A | 1/1969 | Asahina | |
| 4,526,592 A * | 7/1985 | Armbruster | 96/121 |
| 4,901,194 A | 2/1990 | Steinman et al. | |
| 5,055,963 A | 10/1991 | Partridge | |
| 6,063,343 A * | 5/2000 | Say et al. | 422/186.3 |
| 6,508,982 B1 | 1/2003 | Shoji | |
| 6,589,489 B2 * | 7/2003 | Morrow et al. | 422/186.3 |
| 6,773,477 B2 * | 8/2004 | Lindsay | 55/385.3 |
| 7,892,501 B2 | 2/2011 | Parker et al. | |
| 8,080,203 B2 * | 12/2011 | First et al. | 422/24 |
| 2005/0244309 A1 * | 11/2005 | Wang | 422/186.3 |
| 2006/0086252 A1 * | 4/2006 | Huang | 96/134 |
| 2007/0253860 A1 | 11/2007 | Schroder | |
| 2008/0286163 A1 * | 11/2008 | Garfield et al. | 422/120 |
| 2009/0169438 A1 | 7/2009 | Bruggink | |
| 2010/0135850 A1 | 6/2010 | Helenius | |
| 2011/0000251 A1 | 1/2011 | Oka et al. | |
| 2011/0128738 A1 | 6/2011 | Kamii et al. | |
| 2011/0150710 A1 | 6/2011 | Tsuda et al. | |

OTHER PUBLICATIONS

PCT, International Search Report and Written Opinion of the International Searching Authority, in International application No. PCT/US13/21544, dated Mar. 12, 2013. (13 pages).
Haatz "Ion Cluster" webpage, archived Sep. 17, 2007, entire document URL:http://web.archieve.org/web/20070917045750/http://www.haatz.com.kr/eng/hood_option_05.

* cited by examiner

*Primary Examiner* — Kishor Mayekar
(74) *Attorney, Agent, or Firm* — McAndrews, Held & Malloy, Ltd.

(57) ABSTRACT

A system for infusing ion clusters into a target environment includes a housing, a fan, and an ion cluster generation component. The housing has intake and outflow openings. The fan forces air through the intake opening and along a route. The interior surface areas of the housing adjacent to the route are electrically insulating. The route can take either a first path or a second path. The first path goes along a straight path from the fan, through the ion cluster generation component and through the outflow opening. The second path goes along a first segment and a second segment. The first segment runs from the fan and through the ion cluster generation component. The second segment runs from the end of the first segment and extends downwardly through the outflow opening.

13 Claims, 5 Drawing Sheets

TECHNIQUES FOR INFUSING ION CLUSTERS INTO A TARGET ENVIRONMENT

RELATED APPLICATIONS

This application claims the benefit of U.S. Design patent application No. 29/383,237 filed on Jan. 14, 2011 which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Generally, this application relates to air quality improvements. In particular, this application relates to techniques of infusing ion clusters into a target environment to improve air quality.

One type of air purification technique is called photo-catalytic oxidation ("PCO"). This technique may employ PCO devices that generate ions. Such ions may have bactericidal properties, and therefore may be useful for removing bacteria, molds, viruses, or other microbes. The ions may be generated when an ultraviolet light impinges on a photo catalyst, such as $TiO_2$.

PCO devices may be used to improve air quality using passive or active techniques. A passive technique may involve drawing air from a target environment into proximity with a photo-catalytic device. If the environment is relatively large, it may take a relatively long time to improve the air quality of the environment. As another example, it may not be feasible for all of air in a room to be drawn into a passive system. This may leave a certain percentage of microbes. Also, a passive system cannot damage or destroy microbes on surfaces in a room.

An active technique may involve moving the ions away from a PCO device and into a target environment. Assuming there is a sufficient quantity of ions infused into the target environment, such an active technique may be able to improve air quality in a relatively short time. In order to perform such an active technique, it may be desirable to have a relatively strong airflow to cause a sufficient ion infusion into the target environment.

One type of ion generated by a PCO device may be an ion cluster. Ion clusters may hold a relatively large amount of charge that can be effective for damaging or destroying microbes. Such ion clusters may also be relatively fragile. Certain events, such as turbulence or collisions, may tend to damage or destroy the ion clusters. Another undesirable event may occur when charge is drained from an ion cluster, for example, by contact with a conductive, grounded, or oppositely charged object or surface. Such undesirable effects may be magnified when performing an active technique to improve the air quality of a target environment.

Existing PCO systems may be installed within existing HVAC ducts. Such ducts, however, may be formed from an electrically conductive material that may be grounded. Furthermore, HVAC ducts may be relatively turbulent. The ducts may also have geometries that cause ion clusters to collide into the duct walls. These and other properties of HVAC ducts may reduce the effectiveness of active PCO techniques.

Therefore, it may be useful to provide a PCO system that may reduce these and other undesirable effects.

BRIEF SUMMARY OF THE APPLICATION

According to techniques of the application, a system for infusing ion clusters into a target environment includes a housing, a fan, and an ion cluster generation component. The housing has intake and outflow openings. The housing may have a top portion and a bottom portion connected by a hinge. The fan (for example, a cross-flow blower) may be mounted to the top portion of the housing. The housing may have a sloped area between the ion cluster generation portion and the outflow opening. The housing may mounted within an opening for a 2'×2' ceiling tile.

The fan forces air through the intake opening and along a route. The interior surface areas of the housing adjacent to the route are electrically insulating (for example, the surface areas may be fiberglass).

The route can take either a first path or a second path. The first path goes along a straight path from the fan, through the ion cluster generation component and through the outflow opening. The second path goes along a first segment and a second segment. The first segment runs from the fan and through the ion cluster generation component. The second segment runs from the end of the first segment and extends downwardly through the outflow opening. The sloped area of the housing may direct air along the second segment.

According to techniques of the application, a method for infusing ion clusters into a target environment includes using a fan (for example, a cross-flow blower) to: force air into a housing through an intake opening; and force air along a route within the housing. The housing may have a top portion and a bottom portion connected by a hinge. The housing may have a sloped area between the ion cluster generation portion and the outflow opening. The housing may mounted within an opening for a 2'×2' ceiling tile.

The route takes either a first path and/or a second path. The first path is a straight path from the fan, through an ion cluster generation component, and through an outflow opening in the housing. The second path has a first segment and a second segment. The first segment runs from the fan and through the ion cluster generation component. The second segment runs from the end of the first segment and extends downwardly through the outflow opening. The interior surface areas of the housing adjacent to the route are electrically insulating (for example, fiberglass).

According to techniques of the application, a system for infusing ion clusters into a target environment includes a housing having a top portion and a bottom portion. The housing may be mounted within an opening for a 2'×2' ceiling tile. The top portion has an intake opening that receives forced air. The top portion may couple with a supply duct of an HVAC system. Between the top portion and the bottom portion, there are outflow openings facing different directions (for example, orthogonal directions), which allow the forced air to flow into the target environment. In the housing, there are ion cluster generation components for each outflow opening. The air is directed through the ion cluster generation components, through the plurality of outflow openings, and into the target environment. The system may also have a power bus that provides electrical current to the ion cluster generation components.

Figure 1A:
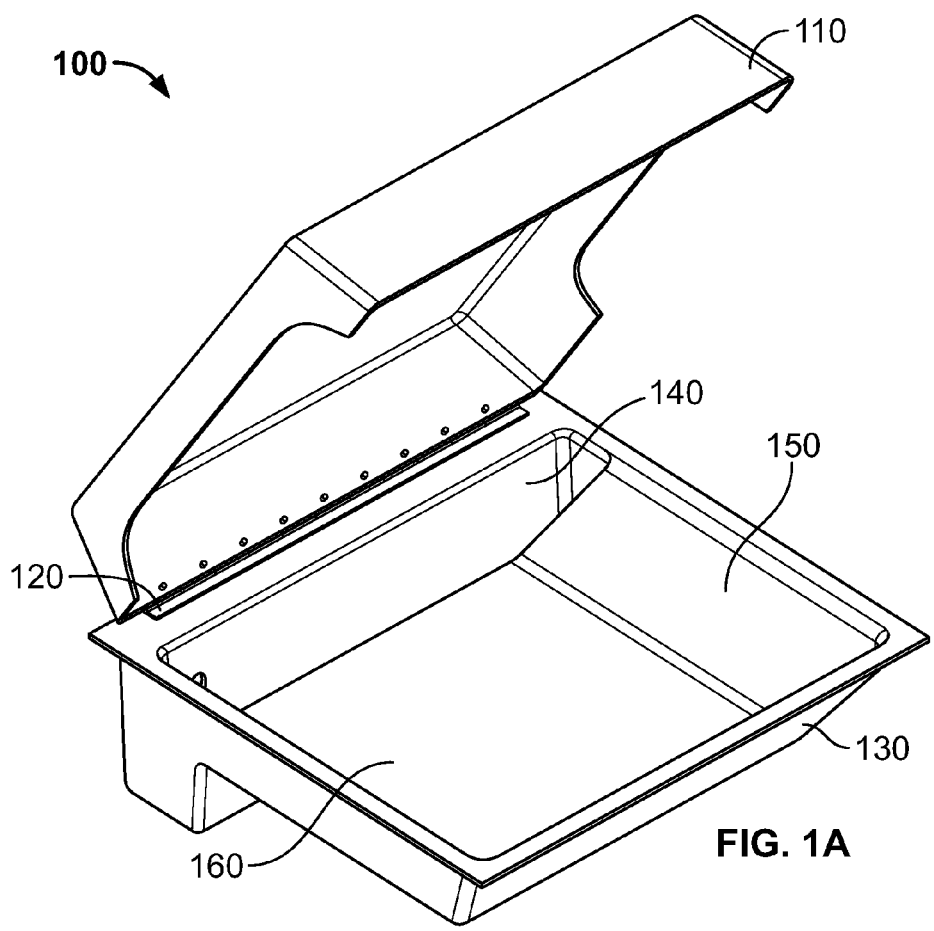
FIGS. 1A-1F illustrate different views of an ion cluster infusing system, according to techniques of the present application.

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE APPLICATION

Figure 1B:
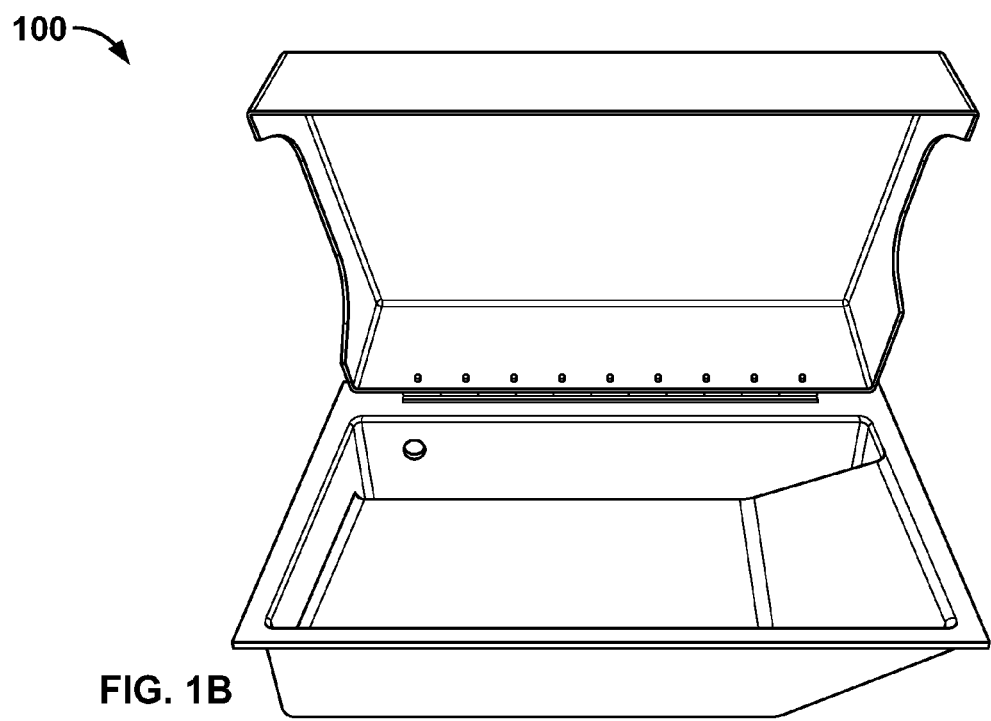
Figure 1C:
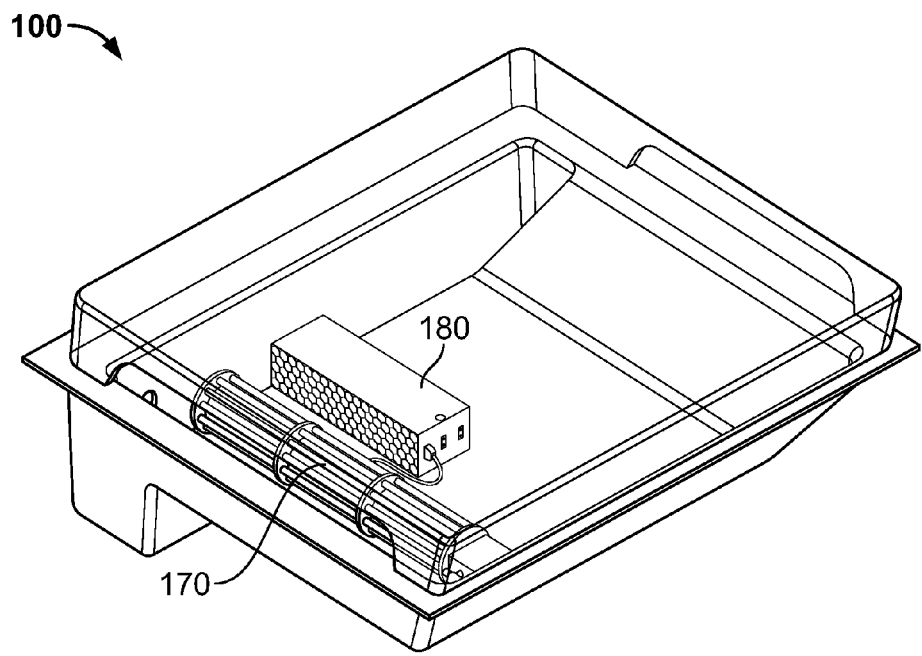

FIGS. 1A-1F illustrate different views of an ion infusing system 100, according to a first technique of the present application. FIGS. 1A-1C show the system 100 upside down to improve the clarity of this application. The system 100 is indicated right-side up in FIGS. 1D-1E.

FIGS. 1A and 1B show a system 100 for infusing ions, such as ion clusters, into a target environment, according to a technique of the present application. The system 100 may have a housing including a bottom portion 110 and a top portion 130. Again, these figures show the system upside down, so the bottom side 110 is depicted as being above the top side 130. The top side 130 and bottom side 110 may be connected by a connector 120, such as a hinge. The top portion 130 may include an upper surface 160, a well portion 140, and a sloped portion 150.

The bottom portion 110 may include cut-away areas. Turning to FIGS. 1E and 1F, it can be seen that such contours of the bottom portion may form openings 112 and 114. As will be further discussed, the opening 112 may be an outflow opening and the opening 114 may be an intake opening. The openings may be different sizes (as shown), may be centered (as shown with opening 114), or may be offset (as shown with opening 112).

FIG. 1C illustrates the system 100 as including a fan 170 and an ion cluster generation component 180. The ion cluster generation component 180 may be a photo-catalytic oxidization ("PCO") device. Other types of PCO devices may include radio-frequency devices, penning traps, plasmatrons, or electron cyclotron resonance devices. The fan 170 may be a cross-flow blower, a bladed fan, or a worm-drive blower.

The top portion 130 may be configured to accept the fan 170 and the ion cluster generation component 180. The well portion 140 may be able to accommodate portions of the fan 170 or the ion cluster generation component 180. The well portion 140 may also accommodate other components, such as a power bus. The fan 170 and the ion cluster generation component 180 may be mounted to the upper surface 160.

Figure 1D:
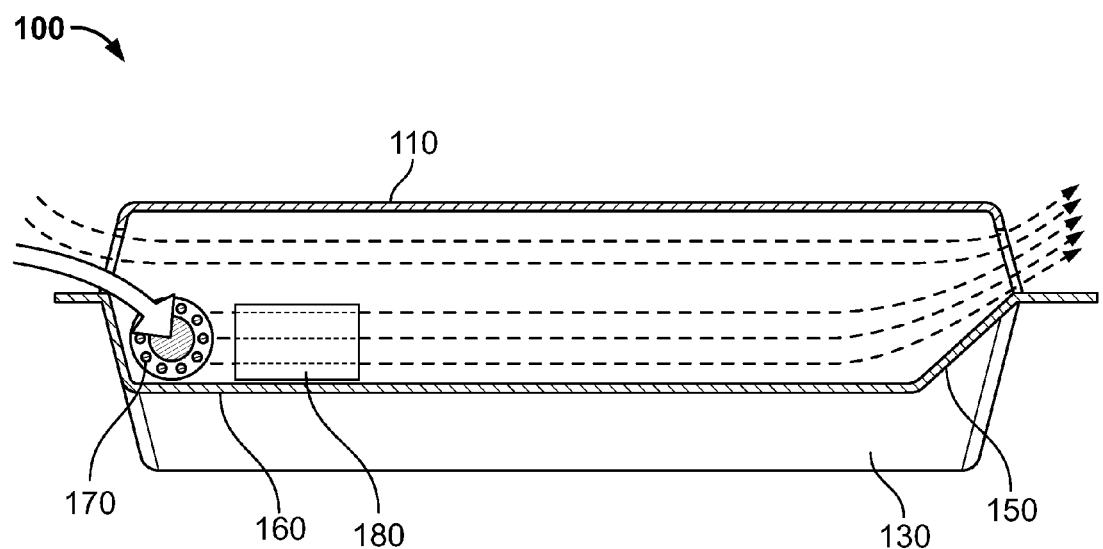
Figure 1E:
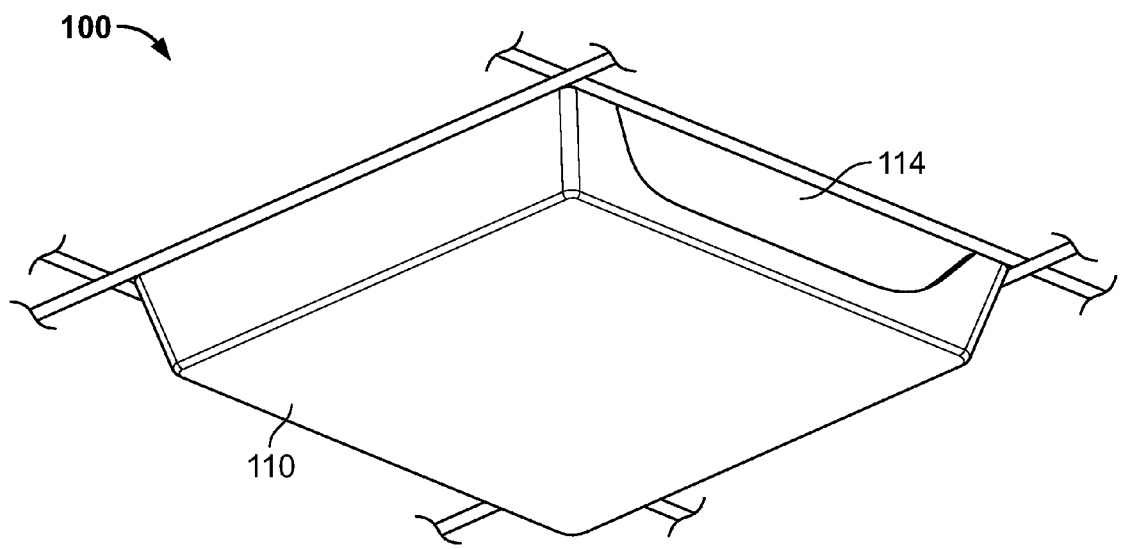
Figure 1F:
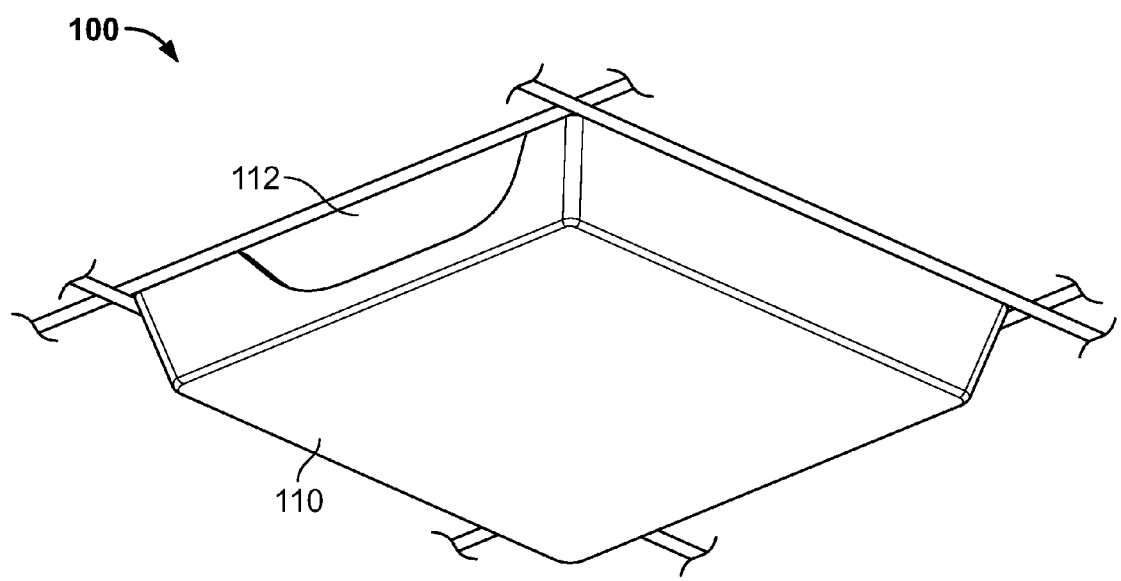

A cross-sectional illustration of the system 100 is shown in FIG. 1D. The dotted lines illustrate the flow of air when the fan 170 is operating. The fan draws or forces (for simplicity, "forces") air in through the intake opening 114. Some of the air passes through the fan 170 and then proceeds along a route. The route may have different possible paths.

One type of path is a substantially straight path. Such a path goes in a substantially straight line from the fan 170, through the ion cluster generation component 180, and through the outflow opening 112. Another type of path has two segments. The first segment goes from the fan 170 and through the ion cluster generation component 180. The second segment extends downwardly from the first segment and goes through the outflow opening 112. The sloped portion 150 may direct the air along the second segment. Other types of paths are also possible, such as paths that do not go through the fan 170 or the ion cluster generation component 180.

The sloped portion 150 may be at a relatively shallow angle (for example, 45° or less). By using a shallow-angled slope portion 150, it may be possible to direct ion clusters downwardly into the target environment without causing undue damage to the ion clusters through collisions or turbulence. The surface areas of the system 100 near the route may be electrically insulating. This may prevent discharge of the ion clusters before they enter the target environment. For example, the top portion 130 and the bottom portion 110 may be made from fiberglass.

FIGS. 1E and 1F illustrate two views of the system 100 when installed in a ceiling. The system is shown as located or mounted in the space for a 2'×2' ceiling tile. The bottom portion 110 may project below the plane of the ceiling. The openings 112 and 114 may sit below the plane of the ceiling. The top portion 130 cannot be seen in FIGS. 1E and 1F because it is located above the ceiling plane in these figures.

Figure 2A:
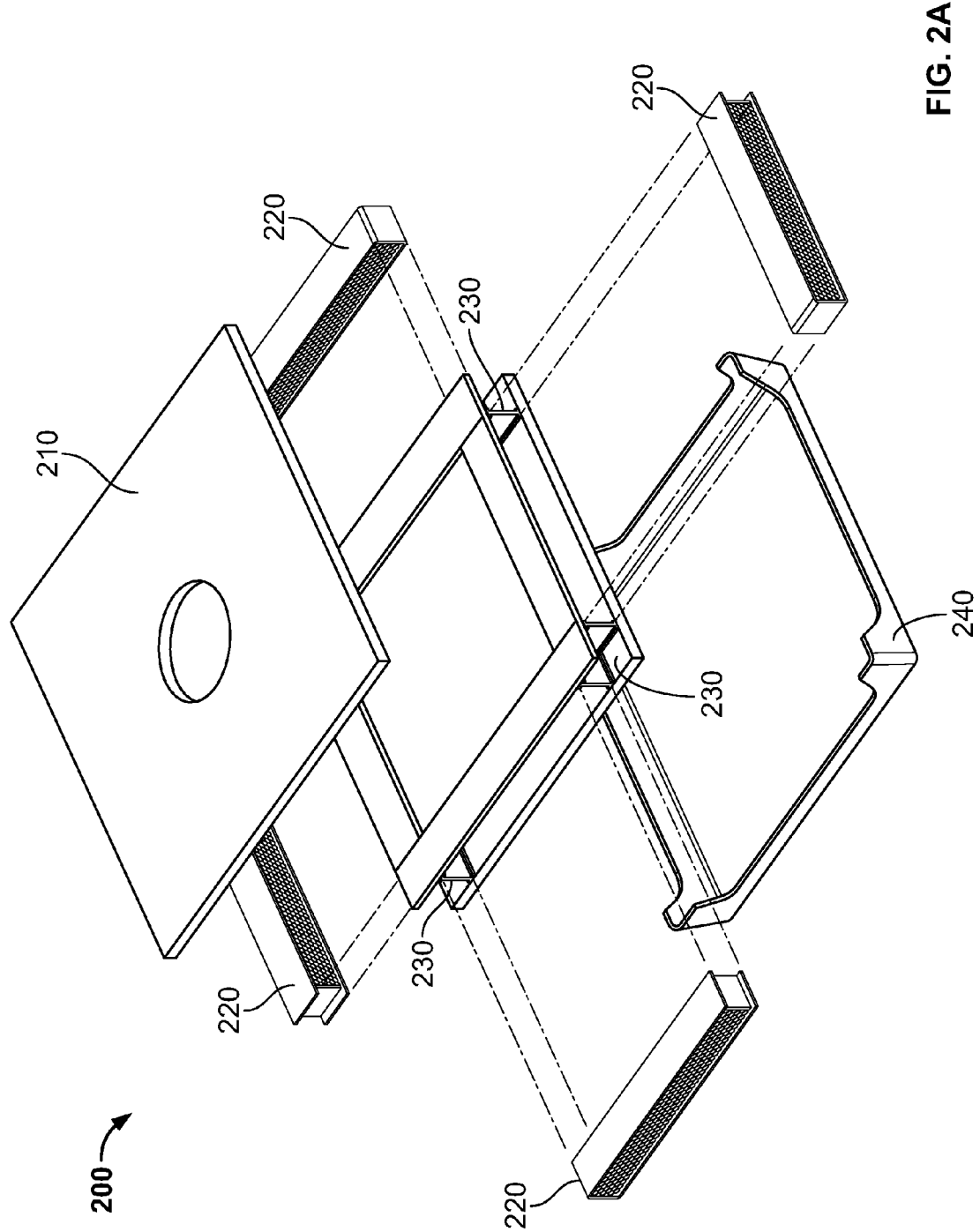
FIGS. 2A and 2B illustrate different views of an ion cluster infusing system, according to techniques of the present application.
Figure 2B:
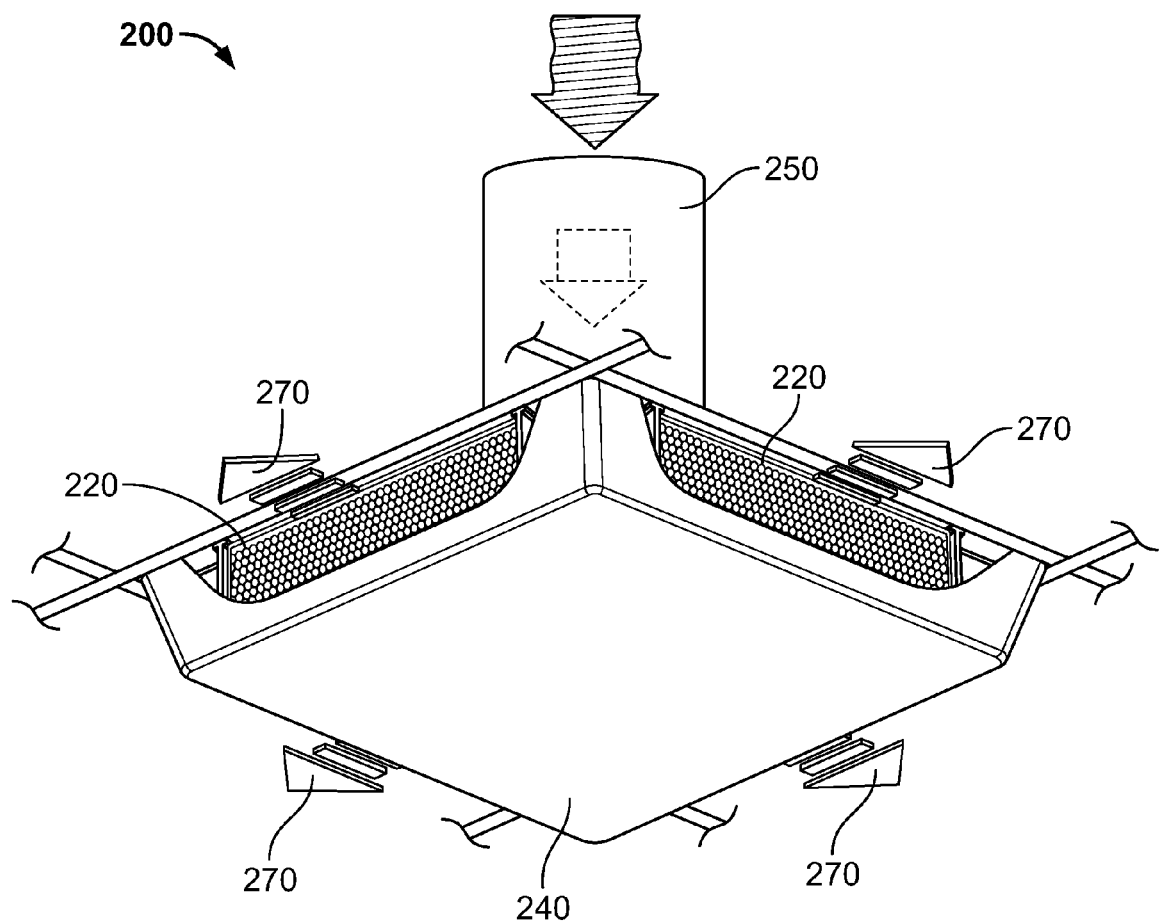

FIGS. 2A and 2B illustrate different views of an ion cluster infusing system 200, according to techniques of the present application. FIG. 2A illustrates an exploded view of the system 200, which may include a housing having a top portion 210 and a bottom portion 240. The housing may also include an intermediate portion 230 between the top portion 210 and the bottom portion 240.

The top portion 210 may have an intake opening. The top portion 210 may coupe to a supply duct of an HVAC system and may receive forced air from the HVAC system through the intake opening. There may be outflow openings between the top portion 210 and the bottom portion 240 or through the intermediate portion 230. These openings may face different directions (for example, directions orthogonal to each other). Ion cluster generation components 220 may be located in the housing, for example, in the intermediate portion 230. There may be one ion cluster generation component 230 for each outflow opening. The system 200 may also include a power bus (not shown) to provide electrical current to the ion cluster generation components 230.

FIG. 2B illustrates the system 200 mounted in a ceiling. For example, the system 200 may be mounted within an opening for a 2'×2' ceiling tile. As shown, forced air enters into the housing from an HVAC supply duct 250. The housing directs the forced air along routes 270 (only a portion of which are shown). The routes 270 pass from the HVAC supply duct, through the ion cluster generation components 220, through the outflow openings, and into the target environment.

Because the ion clusters pass from the components 220 and directly into the target environment, the fragile clusters may not be unduly damaged due to collisions and turbulence. Furthermore, the clusters may not discharge their charges. Also, it may be helpful to use an electrically insulating material (for example, fiberglass) around or on the outflow openings.

It will be understood by those skilled in the art that various changes may be made and equivalents may be substituted without departing from the scope of the novel techniques disclosed in this application. In addition, many modifications may be made to adapt a particular situation or material to the teachings of the novel techniques without departing from its scope. Therefore, it is intended that the novel techniques not be limited to the particular techniques disclosed, but that they will include all techniques falling within the scope of the appended claims.

The invention claimed is:

1. A system for infusing ion clusters into a target environment, the system comprising:
   a housing, the housing having an intake opening and an outflow opening;
   an ion cluster generation component, the ion cluster generation component located in the housing and including an ingress and egress, wherein the ion cluster generation component is configured to generate ion clusters;
   a fan, the fan configured to draw a fluid through the intake opening into a fluid flow path and cause the fluid to flow along the fluid flow path through the ion cluster generation component and through the outflow opening such that the fluid carries ion clusters through the outflow opening; and
   wherein:
      the fluid flow path is in a substantially unchanged direction along a continuous path from the fan, through the ingress of the ion cluster generation component, and through the egress of the ion cluster generation component;
      the fluid flow path from the egress of the ion cluster generation component and the outflow opening is unobstructed;
      interior surface areas of the housing adjacent to the fluid flow path are electrically insulating;
   the fluid flow path includes a first segment, which is straight, and extends from the fan through the ion cluster generation component and a second segment that extends from an end of the first segment extending downwardly through the outflow opening; and
   the housing includes a sloped area between the ion cluster generation component and the outflow opening and the sloped area is configured to direct air along the second segment of the fluid flow path.

2. The system of claim 1, wherein the interior surface areas of the housing adjacent the fluid flow path comprise fiberglass.

3. The system of claim 1, wherein the fan comprises a cross-flow blower.

4. The system of claim 1, wherein the housing comprises a top portion and a bottom portion connected by a hinge.

5. The system of claim 4, wherein:
   the fan and the ion cluster generation component are mounted to the top portion.

6. The system of claim 1, wherein the housing is configured to be mounted within an opening for a 2'×2' ceiling tile.

7. The system of claim 1, wherein the fluid comprises air.

8. A method comprising:
infusing ion clusters into a target environment by:
drawing, with a fan, fluid into a housing through an intake opening;
forcing, with the fan, the fluid along a fluid flow path within the housing to carry the ion clusters into the target environment through an outflow opening in the housing;
wherein:
   a portion of the fluid flow path comprises a path from the fan through an ingress of an ion cluster generation component, through an egress of the ion cluster generation component, and through the outflow opening in the housing;
   the fluid flow path is in a substantially unchanged direction along a continuous path from the fan, through the ingress of the ion cluster generation component, and through the egress of the ion cluster generation component;
   the fluid flow path from the egress of the ion cluster generation component and the outflow opening is unobstructed;
   interior surface areas of the housing adjacent to the fluid flow path are electrically insulating;
   the fluid flow path includes a first segment, which is straight, and extends from the fan through the ion cluster generation component and a second segment that extends from an end of the first segment extending downwardly through the outflow opening; and
   the housing includes a sloped area between the ion cluster generation component and the outflow opening and the sloped area is configured to direct air along the second segment of the fluid flow path.

9. The method of claim 8, wherein the interior surface areas of the housing adjacent to the fluid flow path comprise fiberglass.

10. The method of claim 8, wherein the fan comprises a cross-flow blower.

11. The method of claim 8, wherein the housing comprises a top portion and a bottom portion connected by a hinge.

12. The method of claim 11, wherein:
   the fan and the ion cluster generation component are mounted to the top portion.

13. The method of claim 8, wherein the fluid comprises air.

* * * * *